United States Patent [19]

Englaender et al.

[11] 4,178,295
[45] Dec. 11, 1979

[54] METHOD OF PREPARING PHTHALIDE

[75] Inventors: Fritz Englaender, Bonn-Bad Godesberg; Fritz Robert Kappler, Troisdorf, both of Fed. Rep. of Germany

[73] Assignee: Dynamit Nobel Aktiengesellschaft, Troisdorf, Fed. Rep. of Germany

[21] Appl. No.: 902,201

[22] Filed: May 2, 1978

[30] Foreign Application Priority Data

May 10, 1977 [DE] Fed. Rep. of Germany ....... 2720929

[51] Int. Cl.² ........................................... C07D 307/88
[52] U.S. Cl. ............................................. 260/343.3 R
[58] Field of Search ................................. 260/343.3 R

[56] References Cited

U.S. PATENT DOCUMENTS

| 4,113,741 | 9/1978 | Funten et al. ................. 260/343.3 R |
| 4,116,976 | 9/1978 | Englaender et al. ......... 260/343.3 R |

Primary Examiner—Alan L. Rotman
Assistant Examiner—Jane T. Fan
Attorney, Agent, or Firm—Sprung, Felfe, Horn, Lynch & Kramer

[57] ABSTRACT

An improvement in a process for preparing phthalide by reacting chlorophthalide with hydrogen in the presence of a catalyst at a temperature between 50° and 350° C., the improvement residing in carrying out the process in the absence of a hydrogen chloride acceptor, flowing the chlorophthalide continuously in fluid form through a solid catalyst bed in a reactor, passing the hydrogen through in such an excess so as to sweep off the hydrogen chloride formed and withdrawing phthalide in fluid form.

9 Claims, 1 Drawing Figure

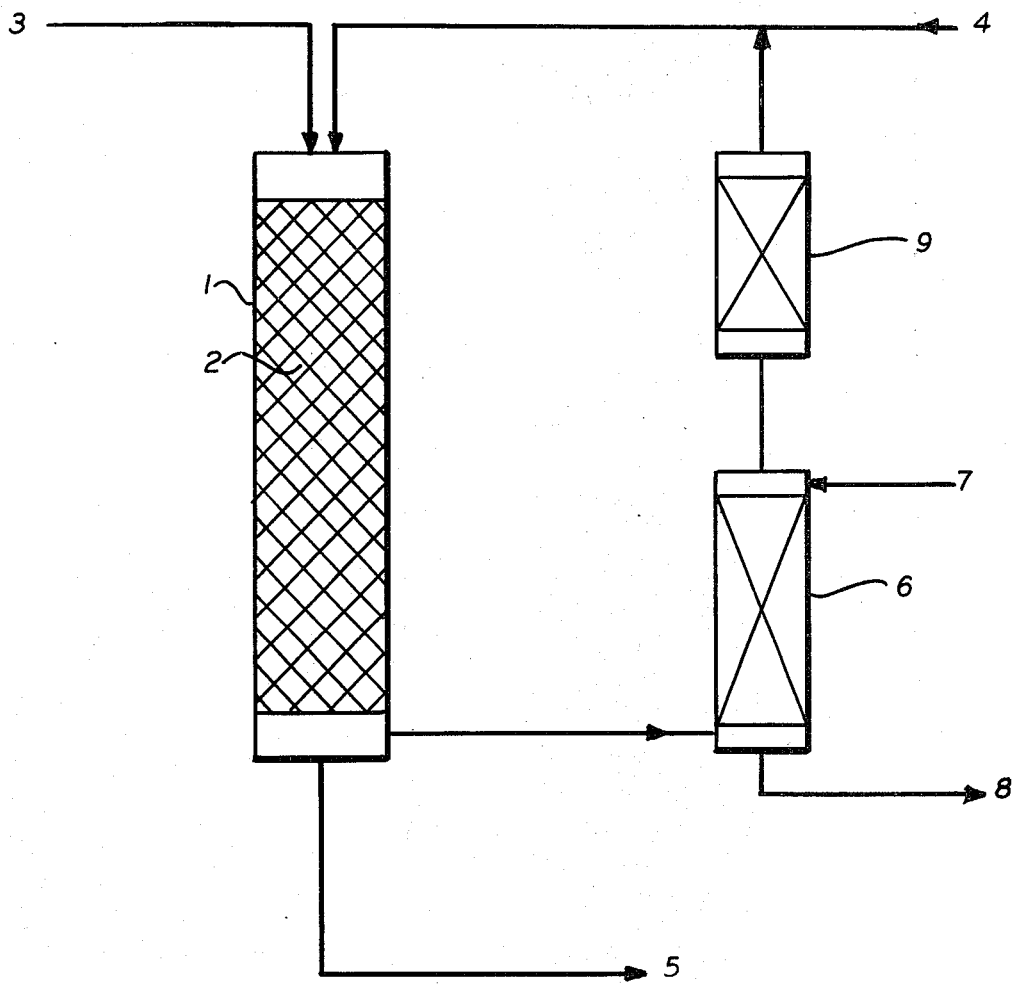

METHOD OF PREPARING PHTHALIDE

BACKGROUND OF THE INVENTION

1. Field of the Invention

This invention is directed to a process for preparing phthalide by reaction of 3-chlorophthalide with hydrogen. More specially, this invention is directed to a process for the synthesis of high quantities of phthalide by a catalytic reaction of 3-chlorophthalide with hydrogen wherein hydrogen chloride which forms as a by-product is effectively removed. The reaction takes place in accordance with the following equation:

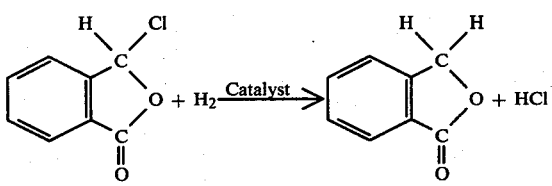

2. Discussion of the Prior

The preparation of phthalide has been performed hitherto either through the reaction of 0-disubstituted benzenes in a plurality of difficult steps with, to some extent, unsatisfactory yields, or through the reduction of phthalic acid anhydride in the presence of catalysts. In these catalytic reactions, the water that forms interferes with the reaction and leads to the formation of undesirable by-products which contaminate the phthalide. These disadvantages are partially avoided in the electrochemical reduction of phthalic acid anhydride or ammonium phthalamale (German OS No. 21 44 419), but the performance of these electrochemical processes generally presents technical difficulties and involves a relatively large investment in apparatus.

The replacement of organically bound halogen with hydrogen, hereinafter referred to as hydrogenolysis, in the presence of catalysts of Group VIII of the Periodic System is also known in itself. In this process, aromatically bound halogen is more easily substituted than aliphatically bound halogen. In all cases the reaction takes place all the more easily the less acid the reaction solution is. However, since hydrogen chloride is released in the hydrogenolysis, known hydrogen chloride acceptors are generally added to the reaction mixture to improve the reaction rate and the space velocity.

The addition of acid-binding compounds of this kind, such as, for example, amines, sodium acetate, and alkail-containing methanol, has nevertheless the disadvantage of complicating the working up of the reaction product and of the catalyst. In particular, the recovery of the catalyst essential to the process can be accomplished only by a plurality of procedures, so that such a method of preparation is not technically feasible.

Another method of intercepting the hydrochloric acid consists in performing the hydrogenolysis in the presence of a solvent having a high dissolving power for hydrogen chloride. Methanol, for example, is suitable as such a solvent in the hydrogenolysis of benzyl chloride to toluene.

If it is desired to apply this method of hydrogenolysis in the presence of methanol to the preparation of phthalide from 3-chlorophthalide, however, several disadvantages are encountered. The phthalide reacts further in the presence of hydrogen chloride and methanol with the cleavage of the lactone ring to form o-hydroxymethylbenzoic acid ester, o-chloromethylbenzoic acid ester and o-toluic acid methyl ester, so that phthalide is produced in a yield of only 15 to 18%.

It has also been proposed to react molten or dissolved chlorophthalide catalytically with hydrogen at elevated temperatures in the absence of a hydrogen chloride acceptor, allowing the gaseous hydrogen chloride to escape from the reactor. The disadvantages of this proposal are evident. If a catalyst supported on a support material of the conventional kind is used, the catalyst has to be kept in a quasi-homogeneous suspension in the liquid phase under the conditions of the reaction and must be vigorously mixed with the hydrogen phase in the reaction vessel by stirring. In order to be able to achieve this quasi-homogeneous suspension of the catalyst grains, a grain size spectrum of from 0.05 to 0.3 mm is indicated for the catalyst. Now, the required vigorous mixing of the liquid and gas phase in the reactor brings about a comminution of the catalyst grains. Furthermore, catalyst losses occur during the filatration of the catalyst from the reaction product. Operation with granular catalyst in the sump phase is therefore uneconomical due to the catalyst losses which occur during the necessary filtration. If one operates without solvent, the difficulties that are involved in the filtration increase.

SUMMARY OF THE INVENTION

It is an object of this invention, therefore, to provide a method of preparing phthalide from chlorophthalide by hydrogenolysis such that phthalide will be produced without a hydrogen chloride acceptor, without catalyst losses, and without special process steps for the separation of catalyst and/or by-products, with a very complete conversion of the chlorophthalide.

In accordance with the present invention, the solutions to the above-recited problems are solved by an improved process for preparing phthalide by contacting chlorophthalide with hydrogen in the presence of a catalyst at a temperature between 50° C. and 350° C., the improvement comprising passing the chlorophthalide through a reactor containing said catalyst fixedly disposed, passing hydrogen therethrough in an amount and at a rate sufficient to sweep out hydrogen chloride formed by said reaction and withdrawing phthalide so formed in fluid form.

In accordance with the present invention, chlorophthalide is reacted in a liquid form, i.e., either in the form of molten chlorophthalide or in the form of dissolved chlorophthalide. The reaction is conducted at a temperature between 50° and 350° C., preferably between 80° C. and 180° C. in the presence of fixedly disposed catalysts. Preferably, the process is carried out in the absence of a hydrogen chloride acceptor.

The hydrogen which is introduced in the reactor is generally employed in a greater-than stoichiometric amount and in some cases is employed in great excess. The hydrogen is employ at such an amount and at such a rate so as to sweep out hydrogen chloride formed as by-product of the reaction. The hydrogen also acts as an interceptor of reaction heat. Phthalide is formed by such a reaction in high yields and is withdrawn continuously from the reactor in fluid form, i.e., in the form of molten phthalide or in the form of phthalide dissolved in an inner solvent.

The grain size of the catalyst is between about one and twelve millimeters.

It is not necessary that the catalyst fill up the entire interior of the reactor. It must, however, be present in such an amount that its catalytic action will suffice for the amount of the chlorophthalide in the reactor.

Suitable catalysts are the noble metals of Group VIII of the Fifth and Sixth Period of the periodic system, which are also called the platinum metals, examples being rhodium, ruthenium or platinum. The metal is used on a support, which contains from 0.1 to 10%, preferably 1 to 2%, of the metal. It is also possible, however, to use support material having a higher or lower metal content. Granulated charcoal or kieselgur, for example, serve as support material. The preferred support material is granulated charcoal.

It is furthermore of considerable importance to the method that the hydrogen be used in an excess. The excess must be at least so great that the gases leaving the reactor will contain hydrogen. The amount of hydrogen to be put in per unit of time is therefore always greater than the stoichiometric amount needed according to the above-given reaction equation.

If both the chlorophthalide (in the molten state) and hydrogen are fed into the reactor from the top at temperatures of 80° to 180° C., the mass velocity for the gas phase (hydrogen+HCl formed) is generally between 10 and 100 kilograms per square meter per hour. The corresponding mass velocity for the liquid phase (the molten chlorophthalide and/or the molten phthalide) is between 100 and 2000 kilograms per square meter per hour.

The method of the invention is distinguished by a high space velocity and by a quantitative reaction of the chlorophthalide. The phthalide obtained by an optimum conduct of the reaction has a purity of over 98%. In general, the percentage of the by-product is less than 4%. The crude phthalide is easily separated from these by-products by fractional distillation or by other known measures.

The hydrogen leaving the reactor contains the hydrogen chloride that forms in the reaction. It can be separated therefrom by simple, known measures. Then, after scrubbing and drying, it is recycled to the process.

In continuous operation, chlorophthalide is fed into the reactor in the amounts per unit of time which correspond to the phthalide withdrawn.

In particular, the feeding of substances to the reactor can be performed in a number of variant ways. Molten chlorophthalide can be proportioned into the upper part of a vertical reactor and trickled through the catalyst bed. In such a case, the hydrogen is fed through the free interstices in the same direction or in the opposite direction from the chlorophthalide feed. It is also possible, however, to force the liquid phase into the reactor bed from the bottom together with hydrogen.

In all these variants, the chlorophthalide can also be used in dissolved form. Suitable solvents are all those which do not react under the conditions of the reaction with chlorophthalide, phthalide, hydrogen chloride and hydrogen. Examples of such solvents are toluene and other aromatic hydrocarbons.

Surprisingly, in none of the above-described variants do by-products form which are difficult to separate, particularly when great excesses of hydrogen are used with respect to the percentage content of the hydrogen chloride being transported away by it.

BRIEF DESCRIPTION OF THE DRAWING

Referring to the accompanying drawing, the same is a schematic flow diagram showing one method for carrying out the process of the invention.

DESCRIPTION OF SPECIFIC EMBODIMENT

Referring to the accompanying drawing, a reactor 1 is charged with fixedly disposed catalyst 2. Into the reactor 1 there is introduced molten 3-chlorophthalide through conduit 3 and hydrogen through conduit 4. Liquid product (molten phthalide) is withdrawn from the bottom of reactor 1 through conduit 5 while gaseous product comprising hydrogen and hydrogen chloride are taken off from reactor 1 and enter hydrogen chloride absorption column 6 which is fed with scrubbing water through line 7. An aqueous hydrogen chloride solution is withdrawn from hydrogen chloride absorption column 6 via conduit 8. Unabsorbed gases rise from hydrogen chloride absorption column 6 and enter the drying tower 9 where water is removed therefrom. This permits recycle of the hydrogen gas to the reactor 1.

The advantages of the method of the invention over the state of the art are obvious. In a simple reaction, which can be performed with or without pressure, chlorophthalide is converted to phthalide of high purity in a single pass through the reactor, and can be used directly for any application. The catalyst losses which occur in filtration are avoided. Even after several days of operation the catalyst does not lose its activity. The hydrogen chloride that is formed is withdrawn from the hydrogen circuit of the process in the form of aqueous hydrochloric acid. The working temperatures and rates of reaction can easily be optimized by known measures.

In order to more fully illustrate the nature of the invention and a manner of practicing the same, the following examples are presented. Where numbers are used in the examples following reference to a reactor conduit or the like these refer to the components of the reaction scheme shown in the accompanying drawing.

EXAMPLE 1

In a vertical reactor 1 of 3 cm inside diameter and 1.5 m length, filled with 435 g of catalyst 2 (average grain diameter 3 mm, 2% palladium on granulated charcoal), 0.41 mole per hour of molten 3-chlorophthalide 3 and 220 liters per hour of hydrogen are introduced at the top through a proportioning apparatus. The reaction temperature is adjusted to 85° C. and kept largely constant during the reaction. The reaction product 5 flowing downward from the reactor is collected in a tank. From there it is delivered for refinement by distillation. The gas phase emerging from the bottom of the reator contains hydrogen and hydrogen chloride. The latter is absorbed in a hydrogen chloride absorption column 6 in water which is introduced into the absorption column at 7. The aqueous hydrochloric acid that is produced leaves the column at 8.

The hydrogen freed of hydrogen chloride also passes through a drying tower 9 and is combined with the fresh hydrogen stream 4.

The 3-chlorophthalide conversion amounts to 100%. The phthalide obtained has a purity of 97.3%. The distillation of the raw product yields phthalide with a purity of 99.9%.

EXAMPLE 2

Repeating the procedure described in Example 1, the throughput of molten 3-chlorophthalide is increased to 1.5 moles per hour at 300 liters of hydrogen per hour. The reaction temperature is increased to 115° C.

A complete conversion of 3-chlorophthalide is obtained; the percentage of phthalide contained in the raw product is 96.7%.

What is claimed is:

1. In a process for preparing phthalide by contacting chlorophthalide with hydrogen in the presence of a catalyst at a temperature between 50° and 350° C., the improvement which consists essentially of flowing chlorophthalide continuously in the fluid form through a fixedly disposed solid catalyst bed of grain size 1 to 12 mm, passing a stoichiometric excess amount of hydrogen gas therethrough at such rate so as to sweep off hydrogen chloride formed as a by-product and withdrawing phthalide from said reactor in fluid form and continuously withdrawing hydrogen gas and hydrogen chloride from said reactor.

2. A process according to claim 1 wherein the process is conducted in the absence of hydrogen chloride acceptor.

3. A process according to claim 1 wherein hydrogen and chlorophthalide are introduced together into the top of a vertical reactor and excess hydrogen is withdrawn from the bottom of the reactor together with hydrogen chloride formed during the reaction and at the bottom of said reactor phthalide in fluid form is withdrawn.

4. A process according to claim 3 wherein the reaction is carried out at a temperature of between 80° and 180° C., the mass velocities in the downward flow in the reactor are between 100 and 2000 $kg/m^2 \cdot h$ for the liquid phase and between 10 and 100 $kg/m^2 \cdot h$ for the gas phase.

5. A process according to claim 1 wherein hydrogen is passed through the reactor in counter-current flow to the flow of liquid chlorophthalide and excess hydrogen is withdrawn together with hydrogen chloride from an upper portion of the reactor.

6. A process according to claim 1 wherein hydrogen gas containing hydrogen chloride is removed from said reactor, said hydrogen chloride is removed from said hydrogen by absorption and excess hydrogen is recycled to said reactor.

7. A process according to claim 1 wherein the chlorophthalide is in molten form.

8. A process according to claim 1 wherein said chlorophthalide is in the form of a solution in an inert solvent.

9. A process according to claim 1 wherein the phthalide withdrawn from the reactor is free of catalyst.

* * * * *